(12) United States Patent
Zhai et al.

(10) Patent No.: US 9,807,317 B2
(45) Date of Patent: Oct. 31, 2017

(54) MULTI-SPECTRAL IMAGING METHOD FOR ULTRAWEAK PHOTON EMISSION AND SYSTEM THEREOF

(75) Inventors: Guangjie Zhai, Beijing (CN); Keming Du, Beijing (CN); Chao Wang, Beijing (CN); Wenkai Yu, Beijing (CN)

(73) Assignee: Center for Space Science and Applied Research, Chinese Academy of Sciences (CN)

( * ) Notice: Subject to any disclaimer, the term of this patent is extended or adjusted under 35 U.S.C. 154(b) by 317 days.

(21) Appl. No.: 14/113,250

(22) PCT Filed: Apr. 23, 2012

(86) PCT No.: PCT/CN2012/074536
§ 371 (c)(1),
(2), (4) Date: Oct. 22, 2013

(87) PCT Pub. No.: WO2012/174940
PCT Pub. Date: Dec. 27, 2012

(65) Prior Publication Data
US 2014/0043486 A1    Feb. 13, 2014

(30) Foreign Application Priority Data
Jun. 20, 2011  (CN) .......................... 2011 1 0166471

(51) Int. Cl.
*H04N 5/30* (2006.01)
*G01J 3/28* (2006.01)
(Continued)

(52) U.S. Cl.
CPC .............. *H04N 5/30* (2013.01); *G01J 3/2803* (2013.01); *G01J 3/2823* (2013.01);
(Continued)

(58) Field of Classification Search
USPC ........................... 348/163; 250/226; 356/300
See application file for complete search history.

(56) References Cited

U.S. PATENT DOCUMENTS 6,249,348 B1 * 6/2001 Jung ...................... G01J 1/0411
250/226
6,996,292 B1   2/2006 Gentry et al.
(Continued)

FOREIGN PATENT DOCUMENTS

CN    101509869    8/2009
CN    102353449    2/2012
(Continued)

OTHER PUBLICATIONS

International Search Report for PCT/CN/2012/074536 dated Aug. 6, 2012.
(Continued)

*Primary Examiner* — Jeremaiah C Hallenbeck-Huber
*Assistant Examiner* — Susan E Hodges
(74) *Attorney, Agent, or Firm* — Jack Schwartz & Associates, PLLC

(57) ABSTRACT

An ultra-weak light multispectral imaging method and an ultra-weak light multispectral imaging system, which can realize multispectral two-dimensional imaging of an ultra-weak light object by constituting a linear array from single-photon detectors of all response wavelengths and combining it with light-splitting technology. The ultra-weak light multispectral two-dimensional imaging system realizes high-resolution optical modulation by adopting the compressive sensing (CS) theory and the digital light processing (DLP) technology and using a linear array single-photon detector as a detection element; the ultra-weak light multispectral two-dimensional imaging system comprises a light filter, a first lens (1), a DMD control system, a second lens, a spectrophotometer, a linear array single-photon detector consisting
(Continued)

of a plurality of single-photon detectors with different response wavelengths, and a central processing unit; and the sensitivity of the system can reach the single-photon level. The invention can be widely applied in the fields of biological self-illumination, medical diagnosis, nondestructive material analysis, astronomical observation, national defense and military, spectral measurement, quantum electronics and the like.

2 Claims, 2 Drawing Sheets

(51) Int. Cl.
  *G01J 3/00* (2006.01)
  *G02F 1/01* (2006.01)
  *G01N 21/76* (2006.01)
  *G01J 1/42* (2006.01)
  *A61B 5/00* (2006.01)
  *G01N 21/64* (2006.01)
  *G01J 1/44* (2006.01)

(52) U.S. Cl.
  CPC .......... *G01N 21/763* (2013.01); *A61B 5/0075* (2013.01); *G01J 1/42* (2013.01); *G01J 2001/442* (2013.01); *G01J 2003/2826* (2013.01); *G01N 21/6452* (2013.01)

(56) References Cited

U.S. PATENT DOCUMENTS

| | | | | |
|---|---|---|---|---|
| 7,283,231 | B2* | 10/2007 | Brady | ............. G06T 9/00 356/303 |
| 8,717,484 | B2* | 5/2014 | McMackin | ............ H04N 5/335 348/337 |
| 8,860,835 | B2* | 10/2014 | Kelly | ............... G02B 26/0833 348/222.1 |
| 2006/0043307 | A1* | 3/2006 | Kimura | ............. G01N 21/6428 250/370.01 |
| 2006/0239336 | A1* | 10/2006 | Baraniuk | .............. H04L 25/20 375/216 |
| 2008/0174777 | A1 | 7/2008 | Carron | |
| 2008/0219579 | A1* | 9/2008 | Aksyuk | ................ G02B 26/06 382/248 |

FOREIGN PATENT DOCUMENTS

| | | |
|---|---|---|
| CN | 102393248 | 3/2012 |
| JP | 2000-244933 | 9/2000 |
| JP | 2005-249760 | 9/2005 |

OTHER PUBLICATIONS

Wu, Quinglin et al. Advanced Single Photon Detector Technologies, Progress in Physics, Sep. 2010 vol. 30, No. 3, pp. 296-306, ISSN 1000-0542.

Figueredo, M. et al. Gradient Projection for Sparse Reconstruction: Application to Compressed Sesnsing and Other Inverse Problems ,IEEE Journal of Selected Topics in Signal Processing, Dec. 2007, vol. 1. No. 4, pp. 586-597, ISSN: 1932-4553.

Candes, E. et al. An Introduction to Compressive Sampling, IEEE Signal Processing Magazine, Mar. 2008 vol. 25 No. 2, pp. 21-30 ISSN: 1053-5888.

Duarte., M. F. et al. Single-Pixel Imaging via Compressive Sampling, IEEE Signal Processing Magazine, Mar. 2008 vol. 25, No. 2 pp. 83-91, ISNN: 1053 5888.

* cited by examiner

MULTI-SPECTRAL IMAGING METHOD FOR ULTRAWEAK PHOTON EMISSION AND SYSTEM THEREOF

FIELD OF THE INVENTION

The invention relates to the technical field of ultra-weak light detection, in particular to an ultra-weak light multispectral imaging method and an ultra-weak light multispectral imaging system. Multispectral two-dimensional imaging of an ultra-weak light object is realized by adopting a linear array single-photon detector and light-splitting technology. The invention can be applied in the fields of biological self-illumination, medical diagnosis, nondestructive material analysis, astronomical observation, national defense and military, spectral measurement, quantum electronics and the like.

BACKGROUND OF THE INVENTION

Multispectral imaging is an important technology for acquiring and displaying precise color information, due to the following facts: firstly, a multispectral image contains more spectral information, and secondly, the multispectral imaging technology well overcomes the phenomenon of metamerism. Moreover, multispectral imaging of an ultra-weak light object particularly has a wide application prospect in multiple fields.

A typical ultra-weak light detector is a single-photon detector. The counting type single-photon detector works in a saturation state, with its sensitivity being at a single-photon level, and can acquire photon density images by adopting a statistical method; and for the single-photon detector with the resolution capacity of photon counts which works in a sub-saturation state, the amplitude of the electrical signal output by the single-photon detector varies with the number of detected photons, thereby based on this electrical signal an ultra-weak light image is acquired. Although the spectral response range of the present single-photon detectors cover the bands of infrared, visible light and the like, it is still narrow for onefold single-photon detector, which is generally used for detecting the light at a certain single frequency.

In this case, the single-photon detector realizes two-dimensional imaging based on the compressive sensing (CS for short) theory and the digital light processing technology, and solves the problem that high-quality imaging of an ultra-weak light object is difficult to realize for the reason that the existing array detection technology in ultra-weak light two-dimensional imaging technology is still immature. And it also solves the problems that the imaging time is long and the resolution is restricted by mechanical raster scan precision due to the combination of a point detector and a two-dimensional drive scanning method.

The CS theory proposed by Donoho, E. J. Candès et al., breaks through the traditional linear sampling pattern, and shows that a little portion of the linear random projection of compressive signals contains enough information for reconstructing original signals. According to the spirit of "sampling first and reconstructing subsequently", it is possible to convert two-dimensional signals into one-dimensional signals distributed along with time and to do the sampling by a single detector.

The CS theory comprises two parts, namely compressive sampling and sparse reconstruction.

The compressive sampling is a process for mapping signals to be measured from high-dimensional signals to low-dimensional ones. If $x \in R^n$ is the data to be measured, $y \in R^k$ is observation data, $\Phi \in R^{k \times n}$ is a random projection matrix (k<<n) and $e \in R^k$ is measurement noise, then the compressive sampling process can be described as formula (1):

$$y = \Phi x + e \tag{1}$$

If x is sparse in a transform domain, that is, $\theta = \Psi x$ and $\Psi$ is a sparse transform matrix, then formula (1) is transformed into formula (2):

$$y = \Phi \Psi \theta + e \tag{2}$$

The random projection matrix $\Phi$ is also referred to as a measurement matrix, and is required to satisfy RIP (Restricted Isometry Property). In addition, the more irrelevant $\Phi$ and $\Psi$ is, the smaller the value of the measurement times k required by sampling is, so generally $\Phi$ is designed as a random matrix.

The sparse reconstruction actually means to solve x in formula (1) under the condition that the observation data y and the measurement matrix $\Phi$ are known, which is an ill-posed problem and generally solved by using an optimization method and can be described as formula (3):

$$\min_{x \in R^n} \left( \frac{1}{2} \|y - \Phi x\|_2^2 + \tau \|x\|_1 \right) \tag{3}$$

If x is sparse in some fixed basis, so the reconstruction problem of formula (3) can be described as formula (4):

$$\min_{x \in R^n} \left( \frac{1}{2} \|y - \Phi x\|_2^2 + \tau \|\Psi x\|_1 \right) \tag{4}$$

In formula (3) and formula (4), the first item is a least-square constraint marked as f(x); the second item is a constraint which describes the sparsity of x; and the sum of the two items is a final target function marked as $\phi(x)$.

The digital light processing technology was proposed by Texas Instruments (TI), when combined with digital video or graphical signals, its micro-mirror and lens system can reflect digital images onto a screen or other surfaces. The core of digital light processing technology is a digital light processing chip, namely digital micro-mirror device (DMD for short), which probably is the most precise optical switch in the world now. The DMD comprises a matrix of up to 2 million micro-mirrors installed on hinges, the size of each micro-mirror is smaller than one fifth of the width of human hair, and each micro-mirror can swing in a certain angle range between −12° and +12°. If the two states are marked as 0 and 1, the micro-mirrors are driven to jitter at a high speed between 0 and 1 by using pulse width modulation (PWM), so that an intermediate state can be realized. The DMD and the related precise electronic elements thereof constitute the so-called digital light processing technology.

SUMMARY OF THE INVENTION

An object of the invention is to solve the problems of two-dimensional imaging and multispectral imaging of an ultra-weak light object by adopting a single-photon detector as a point detector and combining single-photon detection technology and light-splitting technology, thereby provide a novel ultra-weak light multispectral imaging method and a new ultra-weak light multispectral imaging system, wherein multispectral two-dimensional imaging of an ultra-weak light object can be realized by constituting a linear array single-photon detector of various response bands and by combining light-splitting technology.

In order to fulfill the first object, the invention provides a novel ultra-weak light two-dimensional imaging method, wherein the ultra-weak light two-dimensional imaging method realizes high-resolution optical modulation by adopting the CS theory and the digital light processing technology and using a linear array single-photon detector as a detection element. The method comprises the following steps:

1) compressive sampling the compressive sampling is realized together by a DMD control system 7, a first lens 1 and a second lens 2, for converting two-dimensional image data into a one-dimensional data sequence so as to complete compressive sampling of signals to be measured, wherein:

the stray light in the ultra-weak light is filtered by a light filter 6, after which the ultra-weak light is imaged at the DMD control system 7 through the first lens 1, and the DMD control system 7 controls the probability that the photons are reflected to the second lens 2 and the second lens 2 controls the focusing of the photons;

after the modulated and convergent ultra-weak light is split by a spectrophotometer 3, the ultra-weak light with different wavelengths is imaged by a linear array single-photon detector 4; and 2) sparse reconstruction the sparse reconstruction is completed by the combination of a central processing unit 5 and the linear array single-photon detector 4, and a photon density image is reconstructed by adopting an optimization algorithm applied to a measurement matrix on the DMD control system 7, thereby solving out a two-dimensional image.

The method specifically comprises the following steps:

1) the compressive sampling is a process for mapping the signals to be measured from high-dimensional signals to low-dimensional ones:

If $x \in R^n$ is data to be measured, $y \in R^k$ is observation data, $\Phi \in R^{k \times n}$ is a random projection matrix (k<<n) and $e \in R^k$ is measurement noise, then the compressive sampling process can be described as formula (1):

$$y = \Phi x + e \quad (1)$$

If x is sparse in the transform domain, that is, $\theta = \Psi x$ and $\Psi$ is a sparse transform matrix, then formula (1) is transformed into formula (2):

$$y = \Phi \Psi \theta + e \quad (2)$$

In the formula, $\Psi$ is a wavelet transform matrix, and $\Phi$ is a Gaussian random matrix;

2) if the value of the measurement times is k, the number of the pixels in the two-dimensional image is n, then the measurement matrix in formula (1) is written as $\Phi = \{\Phi_1, \ldots, \Phi_i, \ldots, \Phi_k\}$, wherein $\Phi_i$ is the $i^{th}$ row of $\Phi$. The columns of the two-dimensional images of size $\sqrt{n} \times \sqrt{n}$ are connected end to end to form an n×1 one-dimensional column vector, and corresponding to x in formula (1), each element of the vector represents the photon density at a corresponding position; in the DMD control system, each micro-mirror has the same resolution and the columns of the micro-mirrors of the DMD control system are connected end to end to form a 1×n one-dimensional row vector, which corresponds to a row in the measurement matrix $\Phi$, wherein each element represents the probability that the photon at a corresponding position is transmitted to the second lens (2);

3) if the measurement period is T and during this period the DMD control system 7 is kept unchanged, the spectrum is separated by a spectrophotometer 3, so as to make light with certain wavelength directly projected onto a single-photon detector with a corresponding wavelength. If the number of the photons detected by the detector corresponding to a certain wavelength in the linear array single-photon detector 4 is N, then N/T is equivalent to the inner product value of the photon density image and the random number array $\Phi_i$ on the DMD control system, corresponding to an element $$y_i = \sum_{j=1}^{n} \Phi_{i,j} x_j$$

of the observation vector y in formula (1), wherein $\Phi_{i,j}$ and $x_j$ are the $j^{th}$ elements of $\Phi_i$ and x respectively. According to the measurement matrix, the DMD control system is modified each time, repeat k times of the measurement procedure, thereby the whole observation data y can be obtained, and so the data for obtaining the spectral image of the object with a certain wavelength is ready;

the spectral images of the object with other wavelengths can be obtained by the same method as well;

4) the sparse reconstruction means to solve x in formula (1) under the condition that the observation data y and the measurement matrix are known, and x is generally solved by using an optimization method and can be described as formula (3):

$$\min_{x \in R^n} \left( \frac{1}{2} \|y - \Phi x\|_2^2 + \tau \|x\|_1 \right) \quad (3)$$

If x is sparse in some fixed basis so, the reconstruction problem of formula (3) can be described as formula (4):

$$\min_{x \in R^n} \left( \frac{1}{2} \|y - \Phi x\|_2^2 + \tau \|\Psi x\|_1 \right) \quad (4)$$

In formula (3) and formula (4), the first item is a least-square constraint and is marked as f(x); the second item is a constraint which describes the sparsity of x; and the sum of the two items is a target function and is marked as $\phi(x)$.

Preferably, the optimization method adopts a sparse reconstruction by separable approximation with discrete wavelet transform (SpaRSA-DWT) algorithm, that is, the estimated value of the next iteration is obtained by performing discrete wavelet transform (DWT) on the estimated value of the current iteration, performing threshold-processing on the transform coefficients and performing inverse DWT on the threshold-processed coefficients, wherein an optimal step factor is calculated in each iteration;

If the threshold-processing function is described as $S(u, v) = \text{sign}(u)\max\{|u|-v, 0\}$, then the algorithm can be descried as:

$$x^{t+1} = \Psi^{-1} \cdot S\left(\Psi\left(x^t - \frac{1}{\alpha}\nabla f(x^t)\right), \frac{\tau}{\alpha}\right)$$

wherein $\alpha_t$ is one changed with the number of iterations, so that $\alpha_t I$ approaches $\nabla^2 f(x)$, that is, $\alpha_t(x^t - x^{t-1}) = \nabla f(x^t) - \nabla f(x^{t-1})$; and the formula is solved by using a least square method, thus obtaining $$\alpha_t = \frac{\|\Phi(x^t - x^{t-1})\|_2^2}{\|x^t - x^{t-1}\|_2^2}.$$

The imaging process of the invention includes two steps, namely compressive sampling and sparse reconstruction, wherein the compressive sampling is a process of converting two-dimensional image data into a one-dimensional data sequence by the combination of a DMD and lenses; and the sparse reconstruction process is a process of solving out a two-dimensional image according to the obtained one-dimensional data sequence.

In order to fulfill the second object, the invention provides a novel ultra-weak light multispectral two-dimensional imaging system, wherein the ultra-weak light multispectral two-dimensional imaging system realizes high-resolution optical modulation by adopting the CS theory and the digital light processing technology and using a linear array single-photon detector as a detection element.

The ultra-weak light multispectral two-dimensional imaging system comprises a light filter 6, a first lens 1, a DMD control system 7, a second lens 2, a spectrophotometer 3, a linear array single-photon detector 4 consisting of a plurality of single-photon detectors with different response wavelengths, and a central processing unit 5, wherein:

the combination of the DMD control system 7, the first lens 1 and the second lens 2 is used for converting two-dimensional image data into a one-dimensional data sequence so as to complete compressive sampling of the signals to be measured, i.e., firstly the stray light in an ultra-weak light is filtered by the light filter 6, and then the ultra-weak light is imaged at the DMD control system 7 through the first lens 1, and the DMD control system 7 controls the probability that photons are reflected to the second lens 2 and the second lens 2 controls the focusing of the photons; and after the modulated and convergent ultra-weak light is split by the spectrophotometer 3, the ultra-weak light with different wavelengths is imaged by the linear array single-photon detector 4; and before the modulated and convergent ultra-weak light is received by the linear array single-photon detector, spectrum separation is realized by the spectrophotometer (comprising various light-splitting devices and apparatuses such as prisms and gratings), which facilitates subsequent detection by the detectors with different response wavelengths, thus the ultra-weak light with different wavelengths can be imaged, i.e., multispectral imaging; and the combination of the central processing unit 5 and the linear array single-photon detector 4 is used to complete sparse reconstruction, and a photon density image is reconstructed according to a measurement matrix on the DMD control system 7 and photon counts on the linear array single-photon detector 4 by adopting an optimization algorithm, thereby solving out a two-dimensional image.

The single-photon detector is a counting type one, for counting the number of photons during a certain period of time, and then calculating the photon number density by using a statistical method and converting the value into the probability of detecting the photons, as a measured value.

The single-photon detector is one with the resolution capability of photon numbers, for acquiring image data according to the amplitude of output electrical signals, and the amplitude of the output electrical signals can be used as the measured value of the photon density.

The spectrophotometer comprises a light collimating part, a light splitting part, an angle measurement part and a luminosity observation and measurement part, for spectral analysis and measurement.

The spectrophotometer is a prism spectrophotometer or a grating spectrophotometer.

The invention has the advantages that, based on the compressed sensing (CS) theory, by performing optical modulation using the digital light processing technology, two-dimensional imaging is performed on a single spectral component of an ultra-weak light object through a point detector by using a single-photon detector as a detection element, and multispectral two-dimensional imaging is performed on the ultra-weak light object by using the linear array single-photon detector, so the structure of the present invention is simple and its sensitivity can reach single-photon level, moreover, its resolution is directly relevant to the DMD whose resolution has already been very high at present; and several detectors constitute a single-photon detector which can respond to multiple wavelengths and so can simultaneously realize multispectral two-dimensional linear array imaging of ultra-weak light.

The invention can be widely applied in the fields of biological self-illumination, medical diagnosis, nondestructive material analysis, astronomical observation, national defense and military, spectral measurement, quantum electronics and the like.

| Reference signs | | |
|---|---|---|
| 1 first lens | 2 second lens | 3 spectrophotometer |
| 4 linear array single-photon detector | 5 central processing unit | |
| 6 light filter | 7 DMD control system | |

DETAILED DESCRIPTION OF EMBODIMENTS

The invention is further illustrated in details in conjunction with the drawings.

Figure 1:
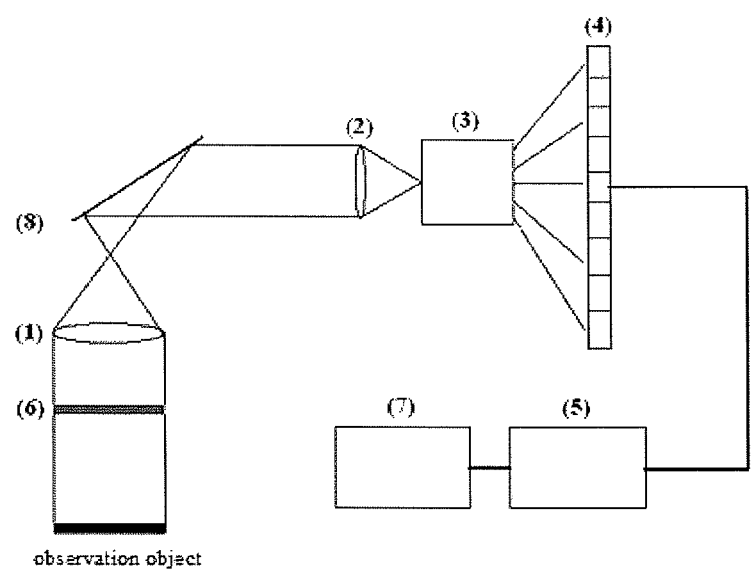
FIG. 1 is a structural diagram of a system provided by the invention.
Figure 2A:
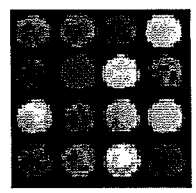
FIG. 2(a)-2(l) are simulation result diagrams of reconstructing a color image by adopting a SpaRSA-DWT algorithm.
Figure 2B:
Figure 2C:
Figure 2D:
Figure 2E:
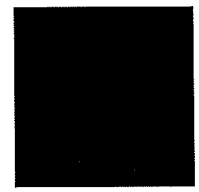
Figure 2F:
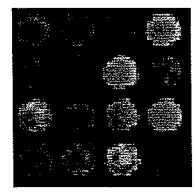
Figure 2G:
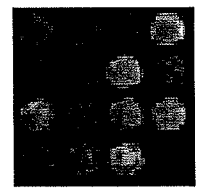
Figure 2H:
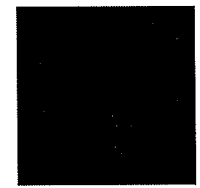
Figure 2I:
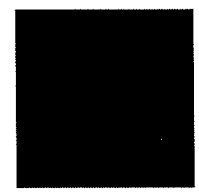
Figure 2J:
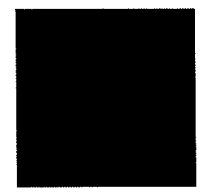
Figure 2K:
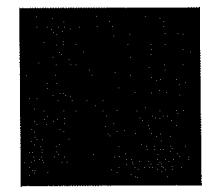
Figure 2L:
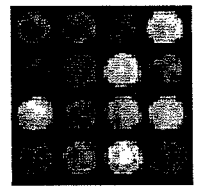

In FIG. 1, the stray light in an ultra-weak light emitted by an observation object is filtered by a light filter 6, after which the ultra-weak light is imaged at a DMD through a first lens 1. The DMD control system 7 controls the probability that photons are reflected to a second lens 2, and then the photons are converged by the second lens 2. If the detector is a counting type single-photon detector, the photons are counted during a certain period of time, and the resulted value is converted into the probability of detecting photons, as a measured value; and if the detector is a single-photon detector with the resolution capability of photon number, then the amplitude of the output electrical signals can be used as the measured value of photon density. Finally, a photon density image is reconstructed by a computer 5 according to the measured value and a measurement matrix on the DMD control system 7 through adopting an optimization algorithm.

In order to facilitate understanding, supposing the value of the measurement times is k, the measurement matrix in formula (1) is written as $\Phi=\{\Phi_1, \ldots, \Phi_i, \ldots, \Phi_k\}$, wherein $\Phi_i$ is the $i^{th}$ row of $\Phi$. The columns of the two-dimensional image of size $\sqrt{n}\times\sqrt{n}$ are connected end to end to form an n×1 one-dimension al column vector, and corresponding to x in formula (1), each element of the vector represents the photon density at a corresponding position; and in the DMD control system, each micro-minor has the same resolution and the columns of the DMD control system are also connected end to end to form a 1×n one-dimensional row vector, which corresponds to a row in the measurement matrix $\Phi$, wherein each element represents the probability that the photon at a corresponding position is transmitted to the second lens 2. If the detector is a counting type single-photon detector, and if the measurement period is T and during this period, the DMD control system is kept unchanged and the number of the photons detected by the single-photon detector is N, then N/T is equivalent to the inner product value of the photon density image and the random number array on the DMD control system; and if the detector is a single-photon detector with the resolution capability of photon number, then the amplitude of the output electrical signals of the single-photon detector is equivalent to the inner product value of the photon density image and the random number array on the DMD control system 7.

The inner product value corresponds to an element $$y_i = \sum_{j=1}^{n} \Phi_{i,j} x_j$$

($\Phi_{i,j}$ and $x_j$ are the $j^{th}$ elements of $\Phi_i$ and x respectively) of the observation vector y in formula (1). According to the measurement matrix, the DMD is modified each time, repeat k times of the measurement procedure, thereby the whole observation data y can be obtained, that is to say, the process of formula (1) is physically realized.

According to photonics knowledge, in an elementary area dA, the probability p(r)dA of observing a photon at a point r at any moment is proportional to the light intensity at that point. Thus, the ultra-weak light image is simulated by a color image of a biochip in simulation experiments. The biochip is a typical ultra-weak light source, and can be conveniently observed mainly by a fluorescent labeling method at present. Actually, all organisms have self-illumination property, and a self-illumination spectrum contains much important information.

In order to verify the feasibility and practicability of the system, the color image of a biochip is regarded as a combination of three primary colors R, G and B in a simulation experiment, for simulating spectral separation. Supposing that the original image is unknown, then it is recovered by adopting the method of the present invention. In the experiment, the resolution of the image is 64×64, and the result as shown in FIG. 2 is obtained by carrying out compressive sampling with a Gaussian matrix and adopting a SpaRSA-DWT sparse reconstruction algorithm, wherein FIG. 2(*a*) shows an original photon density color image;

FIG. 2(*b*) shows a random matrix on the DMD in one-time measurement, wherein black points represent 0, white points represent 1, and gray points represent intermediate values; FIG. 2(*c*) shows a component R of the original image; FIG. 2(*d*) shows a component R reconstruction image of the SpaRSA-DWT algorithm; FIG. 2(*e*) shows a component R residual image of the SpaRSA-DWT algorithm; FIG. 2(*f*) shows a component G of the original image; FIG. 2(*g*) shows a component G reconstruction image of the SpaRSA-DWT algorithm; FIG. 2(*h*) shows a component G residual image of the SpaRSA-DWT algorithm; FIG. 2(*i*) shows a component B of the original image; FIG. 2(*j*) shows a component B reconstruction image of the SpaRSA-DWT algorithm; FIG. 2(*k*) shows a component B residual image of the SpaRSA-DWT algorithm; and FIG. 2(*l*) shows a reconstructed color image of the SpaRSA-DWT algorithm, wherein the correlation coefficient between the reconstructed color image and the original image is 0.9783, and the signal-to-noise ratio is 23.95 dB.

Finally, it shall be noted that the embodiments are only used for illustrating the technical solution of the invention, not limitation thereto. While the invention is illustrated in details with reference to the embodiments, it shall be understood by those ordinary skilled in the art that modifications or equivalent replacements made to the technical solution of the invention do not depart from the spirit and scope of the technical solution of the invention and shall be encompassed in the scope of the claims of the invention.

The invention claimed is:

1. A two-dimensional imaging method for high-resolution optical modulation by compressive sensing and digital light processing and using a linear array single-photon detector as a detection element, said method comprising:
   1) compressive sampling by a digital micro-mirror device (DMD) control system, a first lens and a second lens, to convert two-dimensional image data into a one-dimensional data sequence to complete compressive sampling of signals to be measured, wherein the compressive sampling includes
   filtering stray light by a light filter, imaging the light at the DMD control system through the first lens, controlling reflecting photons to the second lens by the DMD control system controlling focusing of the photons by the second lens; and imaging the light with different wavelengths by the linear array single-photon detector; and
   2) completing a sparse reconstruction by a combination of a central processing unit and the linear array single-photon detector to reconstruct the two-dimensional image data and obtain a two-dimensional photon density image, wherein
      i) the compressive sampling further includes mapping the signals to be measured from high-dimensional signals to low-dimensional signals where,
      where $x \in R^n$ is data to be measured, $y \in R^k$ is observation data, $\Phi \in R^{k \times n}$ is a measurement matrix (k<<n) and $e \in R^k$ is measurement noise, the compressive sample precess is $$y=\Phi x+e \tag{1}$$

ii) where a value of measurement times is k, a number of pixels in the two-dimensional image is n, a measurement matrix in formula (1) is $\Phi=\{\Phi_1, \ldots, \Phi_i, \ldots, \Phi_k\}$ wherein $\Phi_1$ is an $i^{th}$ row of $\Phi$ wherein columns of the two-dimensional images of size $\sqrt{n} \times \sqrt{n}$ are connected end to end to form an n×1 one-dimensional column vector, and corresponding to x in formula (1), each element of the n×1 one-dimensional column vector represents a photon density at a corresponding position; in the DMD control system, each micro-mirror has a same resolution and columns of the micro-mirrors of the DMD control system are connected end to end to form a 1×n one-dimensional row vector, which corresponds to a row in the measurement matrix Φ, wherein each element indicates whether the photon at a corresponding position is transmitted to the second lens;

iii) where a measurement period is T and during this period the DMD control system is kept unchanged, light with certain wavelength directly projected onto the linear array single-photon detector with a corresponding wavelength; where a number of the photons detected by the linear array single-photon detector corresponding to a certain wavelength in the linear array single photon detector is N, then N/T is equivalent to an inner product value of the photon density image and measurement number array Φ on the DMD control system, corresponding to an element $$y_i = \sum_{j=1}^{n} \Phi_{i,j} x_j$$

of an observation vector y in formula (1), wherein $\Phi_{i,j}$ and $x_j$ are $j^{th}$ elements of $\Phi_i$ and x respectively; according to the measurement matrix Φ, the DMD control system is modified each time, repeat k times of the measurement procedure, and the whole observation data y; and iv) the sparse reconstruction solves x in formula (1) using the observation data y and measurement matrix Φ determined in steps ii) and iii) above, and x is equal to:

$$\min\left(\frac{1}{2}\|y - \Phi\Psi^{-1}\theta\|_2^2 + \tau\|\Psi^{-1}\theta\|_1\right) \quad (4)$$

where, Ψ is a wavelet transform matrix, θ is a Gaussian random matrix, and τ is a weight.

2. A two-dimensional imaging method of realizing high-resolution optical modulation by compressive sensing and digital light processing and using a linear array single-photon detector as a detection element, said method comprising:

1) compressive sampling
   by a digital micro-mirror device (DMD) control system, a first lens and a second lens, to convert two-dimensional image data into a one-dimensional data sequence to complete compressive sampling of signals to be measured, wherein the compressive sampling includes filtering stray light in an light by a light filter, imaging the light at the DMD control system through the first lens, controlling reflecting photons to the second lens by the DMD control system controlling focusing of the photons by the second lens; and imaging the light with different wavelengths by the linear array single-photon detector; and 2) completing a sparse reconstruction by a combination of a central processing unit and the linear array single-photon detector to reconstruct the two-dimensional image data and obtain a photon density image, wherein x is the data to be measured, and x is solved by a sparse reconstruction with discrete wavelet transform (SpaRSA-DWT) algorithm, the estimated value of the next iteration is obtained by performing discrete wavelet transform (DWT) on an estimated value of a current iteration, performing threshold-processing on transform coefficients and performing inverse DWT on threshold-processed coefficients, wherein a step factor is calculated in each iteration;

where the threshold-processing function is , S(u,v)=sigh (u)max{|u|−v,0}, the SpaRSA-DWT algorithm is $$x^{t+1} = \Psi^{-1} \cdot S\left(\Psi\left(x^t - \frac{1}{\alpha}\nabla f(x^t)\right), \frac{\tau}{\alpha}\right)$$

wherein $\alpha_t$ changes with each iteration according to:
$\alpha_t(x^t - x^{t-1}) = \nabla f(x^t) - \nabla f(x^{t-1})$ and the formula is solved by using a least square method, obtaining $$\alpha_t = \frac{\|\Phi(x^t - x^{t-1})\|_2^2}{\|x^t - x^{t-1}\|_2^2}.$$

wherein S(u,v) is the threshold-processing function;
sign (u) is the signum function of a real number u defined as follows:

$$\mathrm{sign}(u) := \begin{cases} -1, & \text{if } u < 0 \\ 0, & \text{if } u = 0 \\ 1, & \text{if } u > 0 \end{cases};$$

Φ is the measurement matrix;
Ψ is a wavelet transform matrix;
t means in tth iteration; and
τ is a weight.

* * * * *